US008653240B2

United States Patent
Futami et al.

(10) Patent No.: US 8,653,240 B2
(45) Date of Patent: Feb. 18, 2014

(54) THIOSULFONATE COMPOUND, REVERSIBLE CATIONIZATION AGENT FOR PROTEIN AND/OR PEPTIDE, AND METHOD FOR SOLUBILIZATION

(75) Inventors: Junichiro Futami, Okayama (JP); Hidenori Yamada, Okayama (JP); Go Kyuragi, Okayama (JP); Keiichiro Yagi, Okayama (JP)

(73) Assignee: National University Corporation Okayama University, Okayama (JP)

( * ) Notice: Subject to any disclaimer, the term of this patent is extended or adjusted under 35 U.S.C. 154(b) by 0 days.

(21) Appl. No.: 13/636,789

(22) PCT Filed: Mar. 24, 2011

(86) PCT No.: PCT/JP2011/057238
§ 371 (c)(1),
(2), (4) Date: Dec. 3, 2012

(87) PCT Pub. No.: WO2011/118731
PCT Pub. Date: Sep. 29, 2011

(65) Prior Publication Data
US 2013/0096278 A1    Apr. 18, 2013

(30) Foreign Application Priority Data
Mar. 25, 2010    (JP) ................... 2010-070804

(51) Int. Cl.
*C07K 17/00*    (2006.01)
*A61K 38/00*    (2006.01)

(52) U.S. Cl.
USPC .......................................... 530/345

(58) Field of Classification Search
None
See application file for complete search history.

(56) References Cited

U.S. PATENT DOCUMENTS

2009/0187011 A1    7/2009 Nishimura et al.

FOREIGN PATENT DOCUMENTS

| JP | 11-056386 A | 3/1999 |
| JP | 2004-049214 A | 2/2004 |
| JP | 2005-120017 A | 5/2004 |
| JP | 2007314526 A | 12/2007 |
| JP | 2008-115150 A | 5/2008 |
| WO | WO-2008/001888 A1 | 1/2008 |

OTHER PUBLICATIONS

Cassagne et al., C. R. Acad. Sci. Paris, Chimie / Chemistry 4, 2001, 309-314.*
Yamada et al., "An S-Alkylating Reagent with Positive Charges as an Efficient Solubilizer of Denatured Disulfide-Containing Proteins", J. Biochem., 116, 852-857 (1994).
Inoue et al., "A new derivatizing agent, trimethylammoniopropyl methanethiosulphonate, is efficient for preparation of recombinant brain-derived neurotrophic factor from inclusion bodies", Biotechnol. Appl. Biochem. (1998) 28, 207-213.
Wako Pure Chemical Newsletter, Wako Pure Chemical Industries, Ltd., 2000, vol. 68, No. 1, p. 28-30.
Katayama Chemical Industries, Co., Ltd., [retrieved Feb. 17, 2010], internet <URL:http://katayamakagaku.co.jp/products/lifescience/>.

\* cited by examiner

*Primary Examiner* — Marcela M Cordero Garcia
*Assistant Examiner* — Kaipeen Yang
(74) *Attorney, Agent, or Firm* — Novak Druce Connolly Bove + Quigg LLP

(57) ABSTRACT

The object of the present invention is to provide a novel thiosulfonate compound, a reversible cationization agent for protein and/or peptide, which can reversibly cationize a wider range of proteins and peptides with high stability of quality and accuracy and which are useful for a high degree of purification and recovery, as well as, a method for solubilization for protein and/or peptide using the agent.
The present invention is a thiosulfonate compound having three or more cations derived from a quaternary ammonium group within one molecule.

20 Claims, 8 Drawing Sheets

Fig. 2

Yamada *et al.*
J.Biochem. (1994)116,852

Solubility prediction by Solubility Index (SI)

$$SI = \frac{\text{Effective charge}}{\text{The number of hydrophobic residue (Trp, Ile, Phe, Leu)}}$$

SI value in which the solubility of denatured protein is high (1mg/mL or more)

pH ≥ 6

SI = +0.2 or more, or −0.3 or less pH ≤ 3

SI = +0.6 or more

Example of peptide containing three hydrophobic residues (W,I,F,L)

pH ≥ 6

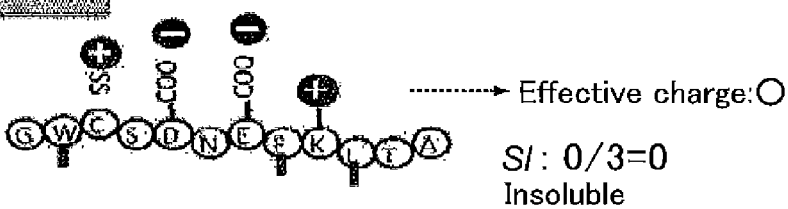

→ Effective charge: 0
SI: 0/3=0
Insoluble pH ≤ 3

→ Effective charge: +2
SI: 2/3=0.66
Soluble

TAPS-Sufonate

Fig. 4
A Confirmation with SDS-PAG
B Evaluation of hydrophobicity with reversed phase HPLC
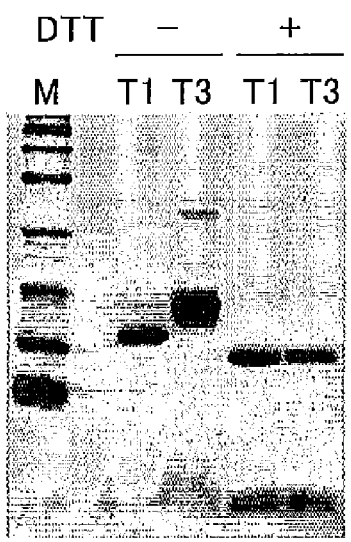
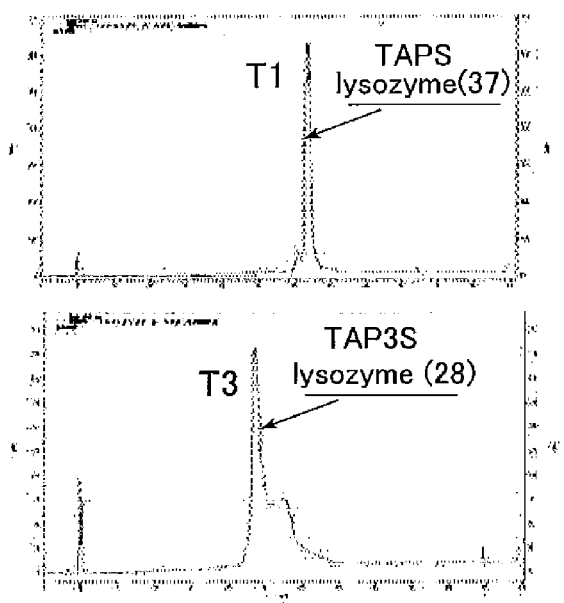
C Confirmation of reversibility of refolding in redox system
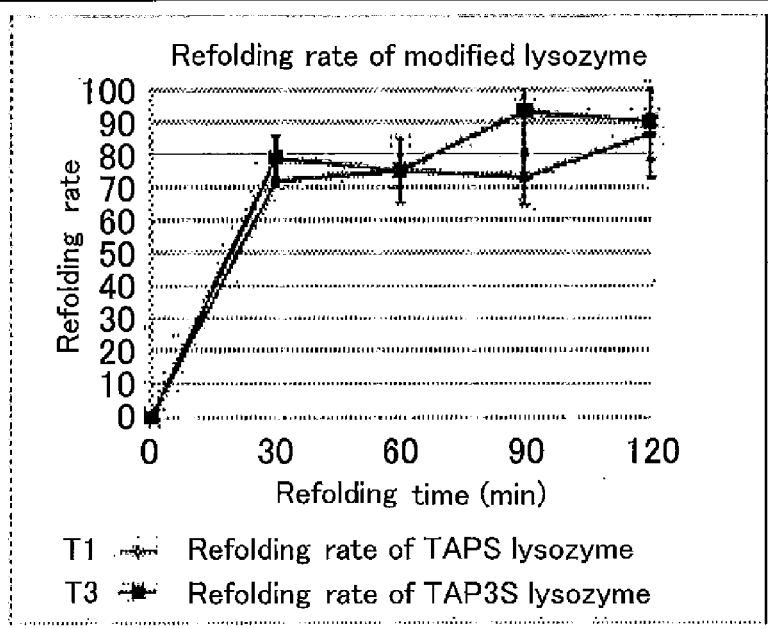

Fig. 7

| Denatured protein | Solubility (mg/ml) | |
|---|---|---|
| | Pure water | Physiological saline |
| Unmodified | 3.2 | 0.7 |
| TAPS-modified | 2.4 → 1.6 | |
| TAP3S-modified | 4.6 → 4.1 | |

Fig. 8
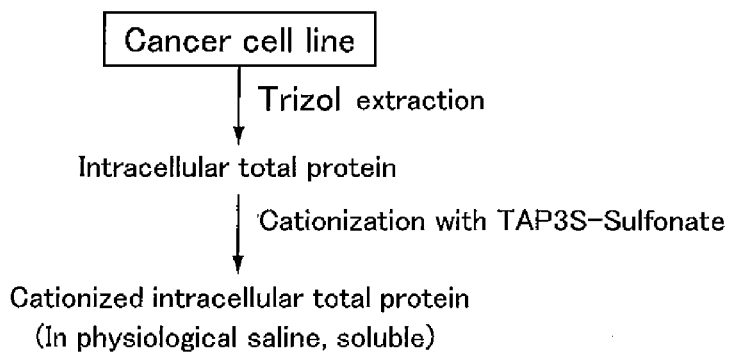
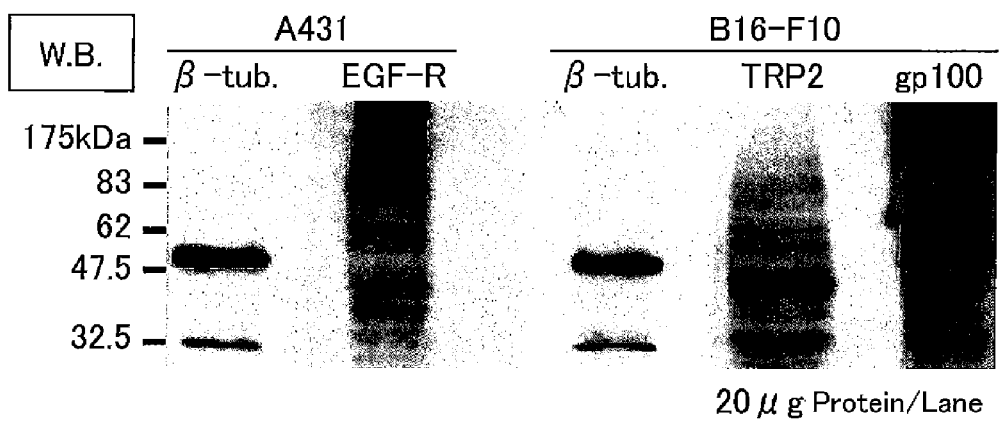
Fig. 9
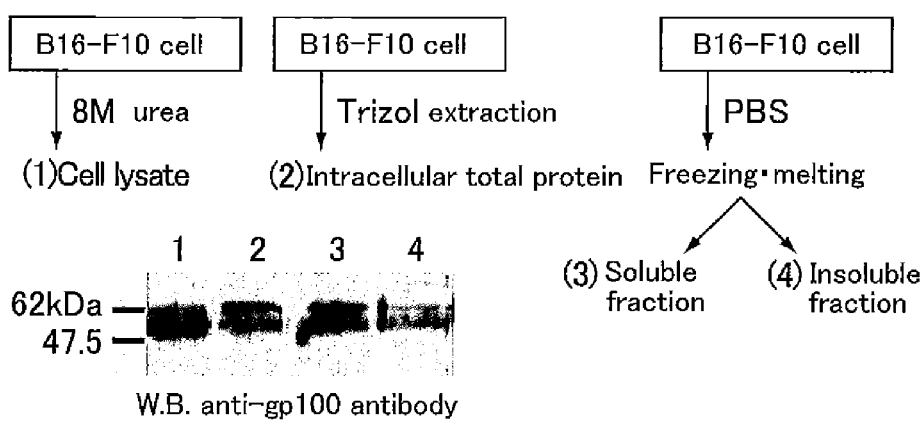

US 8,653,240 B2

THIOSULFONATE COMPOUND, REVERSIBLE CATIONIZATION AGENT FOR PROTEIN AND/OR PEPTIDE, AND METHOD FOR SOLUBILIZATION

CROSS REFERENCE TO RELATED APPLICATIONS

This application is a National Phase filing under 35 U.S.C. §371 of PCT/JP2011/057238 filed on Mar. 24, 2011; and this application claims priority to Application No. 2010-070804 filed in Japan on Mar. 25, 2010 under 35 U.S.C. §119; the entire contents of all are hereby incorporated by reference.

TECHNICAL FIELD

The present invention relates to a thiosulfonate compound, a reversible cationization agent for proteins and/or peptides as well as a method for solubilization. More specifically, the present invention relates to a novel thiosulfonate compound, a reversible cationization agent for protein and/or peptide using the above compound, and a method for solubilization.

BACKGROUND ART

With their tertiary structures often collapsing (denaturing) under non-physiological conditions, proteins and peptides sometimes give rise to precipitations that are insoluble in water. For instance, the molecular mechanism of aggregations of a protein is thought to be one whereby hydrophobic amino acid residues, which are buried inside the molecule for a protein in the native structure, become exposed with denaturation and, with the intermolecular hydrophobic interactions becoming stronger, aggregation is enhanced (refer to FIG. 1, left). As one approach to confer high solubility to a protein with low solubility in water such as a protein in a denatured state, a technique has been developed, whereby a functional group with high hydrophilicity is introduced using chemical modification methods. As this functional group with high hydrophilicity, one processing an electric charge is suitable, and in particular a functional group carrying a positive charge (cation) is advantageous (refer to FIG. 1 right and Non-Patent Literature 1).

At right of FIG. 1, (a) is an example in which an irreversible cationization reagent has been used, in this case, reconstitution (refolding) after solubilization is not possible. In contrast, if a "reversible (denaturing) cationization" technique, which confers a positive charge through a reversible disulfide bond (SS bond), is used on the Cys (cysteine) residues inside the protein, as inside the dotted line at right of FIG. 1 ((b), (c)), it is also possible to dissociate the reagent used in the cationization with a reducing agent as necessary (refer to Non-Patent Literature 2).

As reagents for cationizing a protein reversibly, for instance, TAPS-sulfonate (trimethylammoniopropyl methanethiosulfonate bromide) has been developed and commercialized (refer to Non-Patent Literatures 3 and 4). This reagent can add a univalent quaternary ammonium ion to a protein in denatured state through an SS bond. In addition, derivatives of a polymer having a cationic group (cationic polymer) such as polyethyleneimine (PEI) have been described (refer for instance to Patent Literatures 1 to 3). As PEI derivatives, for instance, PEI-SPDP (mixed reaction reagent of polyethyleneimine and N-succinimidyl-3-(2-pyridylthio)propionate), and the like, are described in Patent Literatures 1 and 2.

CITATION LIST

Patent Literature

Patent Literature 1: Japanese Patent Application Publication No. 2005-120017
Patent Literature 2: Japanese Patent Application Publication No. 2004-049214
Patent Literature 3: Japanese Patent Application Publication No. 2008-115150

Non Patent Literature

Non Patent Literature 1: Journal of Biochemistry, UK, Oxford Univ. Press, 1994, No. 116, p. 852
Non Patent Literature 2: Biotechnology and Applied Biochemistry, USA, Academic Press Inc., 1998, No. 28, p. 207
Non Patent Literature 3: Hidenori Yamada, "Application to protein engineering of TAPS-sulfonate, a novel cationic SH protection reagent—purification and refolding of an exogenous protein having an SS bond produced by *Escherichia coli*—", Wako Pure Chemical Newsletter, Wako Pure Chemical Industries, Ltd., 2000, Volume 68, No. 1, p. 28-30
Non Patent Literature 4: "solubilization of protein from inclusion bodies and refolding adjuvant "TAPS-sulfonate"", [online], Katayama Chemical Industries, Co., Ltd., [retrieved Feb. 17, 2010], internet <URL: http://katayamakagaku.co.jp/products/lifescience/>

SUMMARY OF INVENTION

Problems to be Resolved by the Invention

As mentioned above, a variety of reagents for cationizing proteins reversibly have been developed.

However, being a univalent cationization reagent, TAPS-sulfonate (refer to FIG. 3) can introduce only one cation onto a Cys residue at one location, hence the solubility of proteins in a larger amount may sometimes not be sufficient, from the point of Solubility Index (SI) shown in FIG. 2.

In addition, PEI derivatives described in Patent Literatures 1 and 2, and the like, are thought to be useful in the cationization of proteins with high hydrophobicity (insoluble), as a multitude of cations can be introduced. However, while reagents such as PEI-SPDP are extremely useful for introducing multivalent positive charges, as they are derivatives of macromolecular compounds, the molecular weight and structure (branching degree) are not uniform, and there are problems such as hetero distribution of the electric charge of the protein is formed after cationization, small amounts of SH groups remain as complete cationization is not possible due to steric hindrances. Further, in addition to a quantitative cationization being difficult, there is also a problem that they have a tendency to condense when freeze-dried.

Moreover, while denatured reversibly cationized proteins (that is to say, reversibly cationized denatured proteins) obtained by prior art methods dissolve well in pure water, there is a problem that their solubility is low in physiological salt solutions and culture media that can be used in cell culture, resolution of the problem is desired. Further, while efficient solubilization methods are sought for recombinant proteins expressed in bacterial hosts, total protein extracted in denatured state from living cells (such as cancer cells) or tissues, and the like, such methods have not been established yet. In particular, while effectively solubilizing cancer antigenic proteins is desirable in immunotherapy of cancer, solubilizing the entirety thereof is not straightforward with prior art freeze-thawing method.

The present invention was devised in view of the above situation, and an object thereof is to provide a novel thiosulfonate compound, a reversible cationization agent for protein and/or peptide, which can reversibly cationize a wider range of proteins and peptides with high stability of quality and accurately and are useful for purification and recovery at high degree, as well as, a solubilization method for protein and/or peptide using the above agent.

Means of Solving the Problems

After various studies on reagents that may cationize a protein reversibly, the present inventors and the like, discovered that a thiosulfonate compound having within one molecule three or more cations derived from a quaternary ammonium group was an unprecedented novel compound and could solve aptly the problems described above. Owing to its ability to introduce three or more cations derived from a quaternary ammonium group onto a Cys residue at one location that a protein possesses, such a compound can manifest mainly four action effects below:

(1) solubilization of hydrophobic proteins becomes facilitated, allowing high solubility to be conferred to a wider range of proteins in denatured state.

(2) In the novel compound of the present invention, since structurally the number of cations per molecule is defined and this compound is less likely to be affected by steric hindrance or the like and moreover is enabled to react with the entirety of the Cys residues, the electric charges are allowed for a definite and quantitative treatment and cationization can be carried out by introducing cations onto cysteine residues of proteins and peptides accurately, whereby solubilization is enabled.

(3) Denatured proteins that have been reversibly cationized by conventional methods, while demonstrating high solubility in pure water, do not display sufficient solubility when the ionic strength of the solvent rises. However, cationized denatured proteins obtained by using the novel compound of the present invention demonstrate high solubility even in physiological salt solutions such as physiological saline, and may withstand concentration processes such as freeze-drying.

(4) Using the novel compound of the present invention (preferably in combination with a further high-degree solubilization protocol such as reverse-phase HPLC), it is possible to solubilize intracellular total protein containing no nucleic acids (preferably total intracellular protein in denatured state) reversibly. In addition, as mentioned above in (3), since cationized proteins demonstrate high solubility even in physiological saline, high-purity purification, recovery, and the like, of proteins under physiological conditions are possible. In addition, the cationized proteins may withstand operations such as reversible hydration after freeze-drying.

Further, the present inventors discovered that these action effects were exerted when the compound is applied not only to proteins but also to peptides, and that the novel compound of the present invention was useful as a reagent for reversibly-cationizing proteins and/or peptides, that is to say, a reversible cationization agent for proteins and/or peptides. Particularly among them, the compound is useful as a reversible cationization agent for highly hydrophobic proteins and/or peptides in denatured state, and concretely, for recombinant proteins produced by *Escherichia coli* or the like, total protein and peptide from animal cells, and the like. In addition, this reversible cationization agent is useful as a solubilizer of proteins and/or peptides, and methods for solubilizing a protein and/or a peptide using the solubilizer is an extremely useful technique in fields that handle proteins and/or peptides. With such a technique of the present invention being useful in both basic research and clinical fields such as application to analysis of intracellular proteins and cancer immunotherapy using dendritic cells, it is thought that the application range of chemical research, medical treatments or the like is broad. The technique can be said to have tremendous potentiality and expandability, such as, it may contribute to improving therapeutic effects, for instance, in administration to tissues such as spinal cord, immunotherapy of cancer, or the like, using cancer cells or cancer tissues and dendritic cells, by preparing the target dendritic cell vaccine more efficiently.

That is to say, the present invention is a thiosulfonate compound having within one molecule three or more cations derived from a quaternary ammonium group.

In addition, the present invention is also a reversible cationization agent for reversibly-cationizing a protein and/or a peptide, the reversible cationization agent being a reversible cationization agent for a protein and/or a peptide containing the above thiosulfonate compound.

Further, the present invention is also a method for solubilizing a protein and/or a peptide, the solubilization method being a solubilization method for a protein and/or a peptide using the above reversible cationization agent for protein and/or peptide.

Then, the present invention is also a method for solubilizing a mixture of denatured total protein extracted from a cultured cell and/or a living tissue in a physiological salt solution, the solubilization method being a solubilization method using the above reversible cationization agent for a protein and/or a peptide.

The present invention will be detailed below.

<Thiosulfonate Compound>

The thiosulfonate compound of the present invention is a compound having within one molecule three or more cations derived from a quaternary ammonium group, and, having a thiosulfonate group. In addition, a chemical form having a halogen ion or the like as a paired anion is suitable. The structure of the compound of the present invention can be confirmed by NMR or elemental analysis, or the like.

The thiosulfonate compound is preferably represented by the following general formula (1):

[Chem. 1]

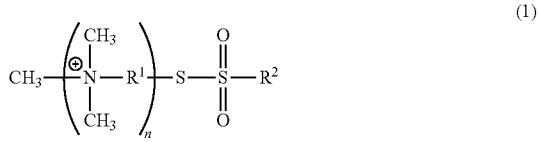

(1)

(wherein $R^1$ may be identical or different from one another and represents an alkylene group having 2 to 20 carbons; $R^2$ represents a lower alkyl group; and n is an integer of 3 or greater.)

In general formula (1), n represents the number of cations derived from the quaternary ammonium group. It is believed that, if this number of cations is excessive, cationizing protein and/or peptide quantitatively becomes difficult due to steric hindrance or the like. Consequently, when using the thiosulfonate compound of the present invention as a reversible cationization agent and a solubilizer, or the like, for a protein and/or a peptide, n is preferably 3 to 10 from the relationship between the quantifiability of the reaction with the protein and/or the peptide and the application range of the solubilizable protein and/or peptide. More preferably, n is 3 to 8, further preferably 3 to 5 and particularly preferably 3.

In addition, $R^1$ in general formula (1) is identical or different from one another, and represents an alkylene group with 2 to 20 carbons. Such an alkylene group may be a straight chain alkylene group or may be either of alkylene groups having branched chain or cyclic chain. When using the thiosulfonate compound of the present invention as a reversible cationization agent, a solubilizer, or the like, for a protein and/or a peptide, it is suitable that $R^1$ is a straight chain alkylene group or a lower alkylene group having a branched chain. This takes into consideration the possibility that, reactivity between the thiosulfonate compound and the protein and/or peptide becomes insufficient due to increasing steric hindrance, thereby influencing usability (for instance, processes such as freeze-drying cannot be used).

Due to the hydrophobicity of the thiosulfonate compound being more elevated with the number of carbon atoms being greater, the alkylene group represented by $R^1$ described above becomes inconsistent with the purpose of a case where the compound is used as a reversible cationization agent, a solubilizer, or the like, for a protein and/or a peptide, that is to say, the purpose of elevating hydrophilicity with cationization, thus, it is suitable that the number of carbon atoms is 10 or less. In addition, also taking stability into consideration, the number of carbons of the alkylene group represented by $R^1$ is selected from 2 to 10, preferably 2 to 6 and more preferably 2 to 4. As $R^1$, a straight alkylene is desirable and a propylene group is particularly desirable. When $R^1$ is different from one another, the bonding order thereof within the structure of the compound represented by general formula (1) is arbitrary.

As the lower alkyl group represented by $R^2$, a methyl group is desirable.

As the molecular weight of the thiosulfonate compound, for instance, to be 300 to 3,000 is suitable. Of this, to be 300 to 2,000 is more desirable, taking steric hindrance or the like into consideration when using the compound as a reversible cationization agent, a solubilizer, or the like, for a protein and/or a peptide. Further desirable is 300 to 1,000.

The molecular weight referred to here is a value calculated as the sum total of the atomic weights of the constituting elements.

In a preparation method (synthesis method) for the thiosulfonate compound, the compound can be obtained, for instance, by reacting an ammonioalkyl halide having one or more cation derived from a quaternary ammonium group within one molecule (for instance, (3-bromopropyl)trimethylammonium bromide and the like) with a trialkyl diamine such as trimethyldiamine or triethyldiamine, then, reacting a dihaloalkane such as dibromopropane, and next, reacting a thiosulfonate salt such as methane thiosulfonic acid sodium salt. The reaction may be carried out by changing the number of cations of the ammonioalkyl halide according to the number of cations derived from the quaternary ammonium group in the target thiosulfonate compound.

<Reversible Cationization Agent for Protein and/or Peptide>

The reversible cationization agent for a protein and/or a peptide of the present invention contains the thiosulfonate compound of the present invention. That is to say, the thiosulfonate compound of the present invention is used in the reversible cationization agent for protein and/or peptide. Compared to conventional reagents, such a reversible cationization agent is extremely efficacious for the reversible cationization of highly hydrophobic denatured protein or peptide. In addition, from the fact that, structurally, the number of cations per molecule is defined, and, the agent is less likely to be affected by steric hindrance or the like, reacting with the entirety of the Cys residues becomes possible. From the fact that, thusly, the reversible cationization agent of the present invention, with the electric charges being defined, allows for a quantitative treatment, cationization by introducing cations onto cysteine residues of protein and peptide accurately, and solubilization become possible. Further, probably related to these advantages, not only solubilization is possible even under conditions other than water, such as physiological saline, where solubilization of denatured protein, highly hydrophobic peptide or the like is difficult, solubilization, purification and recovery from cells or tissues of denatured total protein and peptide containing no nucleic acids are possible in physiological saline. This is to say, the target protein or peptide can be isolated and purified, as necessary by refolding in vitro or intracellularly. Therefore, the application range, such as the studies of the biochemistry, medical treatment, and others, is thought to be broad. For instance, it is thought that contribution to improving therapeutic effects is possible, in administration to tissues such as spinal cord, immunotherapy of cancer, or the like, using cancer cells or cancer tissues and dendritic cells, by preparing the target dendritic cells more efficiently. Particularly in immunotherapy of cancer, while it is desirable to solubilize a cancer antigenic protein efficiently, solubilizing the entirety thereof is not straightforward with conventional freeze-thawing methods. For instance, in the example performed taking as a model in which a mouse melanoma cell was treated by the freeze-thawing method, it was confirmed that approximately 50% of the cancer antigenic protein gp100 became insoluble after freeze-thawing (refer to FIG. 9). It was verified that, if the solubilization technique developed by the present invention is applied to this problem, solubilization of total intracellular protein is possible, and each protein among the EGF receptor, TRP2 and gp100, which may actually become a cancer antigen, can be solubilized in physiological saline, quantitatively (refer to FIG. 8).

As long as it contains the thiosulfonate compound of the present invention, the reversible cationization agent for a protein and/or a peptide of the present invention may further contain or may not contain one, two or more species of constituents other than the thiosulfonate compound.

Here, in the present invention, reversibly-cationizing a protein and/or a peptide means introducing a positive charge through a reversible bond, and, for instance, the form of disulfidizing a mercapto group that a protein and/or a peptide possesses to introduce a positive charge may be cited.

In addition, in the present invention, a protein and/or a peptide means a compound generated by two or more amino acids being bonded by a peptide bond, and for instance, may be a conjugated protein and/or peptide comprising a bonded carbohydrate chain, lipid, phosphate group or the like. As such proteins and/or peptides, for instance, peptides, enzymes, antibodies, and other proteins and/or peptides, or the like, having functionality (biological activity such as medicinal action) and being useful as medicines/drugs can be used, and as the molecular weight thereof, to be 100 to 1,000,000 is desirable.

While the reversible cationization agent can be used in the solubilization of protein and/or peptide in any form, using it in the solubilization of a protein and/or a denatured peptide is suitable. That is to say, it is desirable that the protein and/or peptide to be reversibly cationized by the reversible cationization agent is a denatured protein and/or a peptide (a denatured protein and/or a denatured peptide). This allows the manifestation of the effects described above to be observed more.

As the denatured state, a state in which the inherent tertiary structure corresponding to the natural state (native state) that a protein and/or a peptide molecule exhibits under approximately physiological conditions has been lost without being accompanied by a cleavage of a covalent bond may be cited. As protein and/or peptide in such a state, for instance, protein and/or peptide for which the acquisition of those in native state is difficult; protein and/or peptide for which denaturation/precipitation occurs in the process of cationizing the protein and/or the peptide in order to introduce them into a cell; protein and/or peptide expressed as inclusion bodies in *Escherichia coli* or the like; and the like, may be cited. Among them, to be one having a mercapto group is desirable, and those having a cysteine residue are suitable.

<Protein and/or Peptide Solubilization Method>

In the protein and/or peptide solubilization method of the present invention, the reversible cationization agent for protein and/or peptide is used. It is suitable for the solubilization method particularly to be a method for solubilizing a denatured protein and/or a peptide. That is to say, it is desirable that the protein and/or peptide to be solubilized by the solubilization method is a denatured protein and/or a peptide (a denatured protein and/or a denatured peptide). This allows the manifestation of the effects described above to be observed more. As denaturing agents, for instance, urea and guanidine hydrochloride can be used.

In the solubilization method, it is suitable to react the protein and/or the peptide to be solubilized (the target protein and/or peptide) with the reversible cationization agent. As the amount of reversible cationization agent used in this reversible cationization reaction, it is preferably set so that the reversible cationization agent is at a molar concentration of 1 to 100-fold with respect to the molar concentration of the mercapto groups that the target protein and/or peptide possesses. More desirable is 1.1 to 2-fold.

In the solubilization method, it is also desirable to carry out the reversible cationization reaction in the presence of a denaturing agent and a reducing agent, or, to react a reducing agent after the reversible cationization reaction. As reducing agent, for instance, using DTT (dithiothreitol) and β-mercaptoethanol is suitable. However, when the reversible cationization reaction is carried out in the presence of a reducing agent, adding and reacting 1.1 to 2-fold amounts of reversible cationization agent is desirable, by taking into consideration the total molar concentration of the reducing agent contained in the reaction solution and the mercapto groups that the protein and/or the peptide possesses. In addition, as the temperature when carrying out the reversible cationization reaction, 5 to 40° C. is suitable. More desirable is 25° C.

In addition, with the solubilization method, after the reversible cationization reaction, the reversibly cationized protein and/or peptide can be purified by ordinary techniques such as dialysis and column chromatography. The purification is preferably carried out under acidic conditions. With the disulfide bonds are stabilized sufficiently, and the solubility and yield of the obtained reversibly-cationized protein and/or peptide being improved by carrying out dialysis under acidic conditions, for instance, when introducing the reversibly cationized protein and/or peptide into a cell, activation inside the cell can be carried out easily. In addition, when using a protein and/or a peptide expressed by *Escherichia coli*, contaminants derived from *Escherichia coli* (nucleic acids, sugars and lipids) are readily insolubilized under acidic conditions, allowing subsequent purification to be carried out even more readily. Purifying under the conditions of pH 6 or lower is more desirable.

In addition, when solubilizing the total protein derived from living tissues or cultured cells as materials, it is desirable to have as materials the total protein from which nucleic acids have been removed beforehand by applying the Trizol reagent (phenol/guanidine isothiocyanate, manufactured by Invitrogen) or the like, and the solubilization procedure therefor follows the reversibly-denaturing-cationizing method. While pure water is a desirable solvent for these denatured reversibly cationized proteins, when there is a need for substitution to a physiological salt solution, high solubility can be maintained by devising dialysis procedures and purification methods. For instance, in the event a precipitation has occurred by adding salt in physiological concentrations to a solvent of a denatured reversibly cationized protein dissolved in pure water, redissolving this in a denaturing agent such as urea and guanidine hydrochloride and dialyzing against the physiological salt solution to which substitution is desired allows the solubility with respect to the target salt solution to be increased. In addition, it is also possible to increase the solubility by purifying to high purity using reverse-phase HPLC or the like.

Thusly, using the cationization agent of the present invention allows a protein, or the like, to be solubilized in a variety of salt solutions by applying a multistep protocol comprising combining a plurality of protocols used for the solubilization, purification, and the like, of proteins (for instance, dialysis, HPLC and the like). Such protocols and conditions are known to those of ordinary skill in the art. In addition, the number and combination of protocols are not limited in particular.

In the solubilization method of the present invention, the product may be concentrated by freeze-drying, or the like, in the middle of solubilization or after finishing solubilization. In the freeze-dried case, the obtained product can, as-is, be conserved stably in a reconstitutable state. The freeze-dried product can as necessary be reconstituted with a suitable solvent and used, or purified further. It has been confirmed that if the solubilizer of the present invention is used, there is almost no drop in the quality due to freeze-drying (data not shown).

Further with the solubilization method, the reversible cationization agent may as necessary be dissociated from the reversibly cationized protein and/or peptide. The dissociation of the reversible cationization agent can be carried out using the SH/SS exchange reaction in the presence of a catalyst; in addition, the agent may dissociate spontaneously in the reductive environment within the cytoplasm, or the like.

For instance, when an egg-white lysozyme is used as the protein and/or peptide, while it is desirable to carry out the SH/SS exchange reaction in a solvent in which oxidized glutathione:reduced glutathione=1:4 (molar amount ratio) has been mixed, the reversible cationization agent dissociates in the process of this SH/SS exchange reaction. While the egg-white lysozyme in the active conformation has four sets of SS bonds present within one molecule such that there is the necessity of refolding in the correct combination, since the egg-white lysozyme in the active conformation is to be the structure with the lowest free energy (=stable), the molecule in which, ultimately, the reversible cationization agents having dissociated, the correct four sets of SS bonds have been formed, is to manifest a biological activity. The "refolding rate" in Experimental Example 1 described below has been evaluated with the bacteriolytic activity (enzymatic activity) exhibited by the lysozyme.

As described above, the present invention provides a method for solubilizing a mixture of denatured total protein extracted from a cultured cell and/or a living tissue in a physiological salt solution. In such a solubilization method, using a reversible cationization agent for a protein and/or a peptide containing a thiosulfonate compound having a group represented by the general formula (1) is desirable.

That is to say, a solubilization method, which is a method for solubilizing a mixture of denatured total protein extracted from cultured cells and/or living tissues in a physiological salt solution, which solubilization method uses the reversible cationization agent for protein and/or peptide, is also one among the present invention.

The thiosulfonate compound is preferably a thiosulfonate compound in which $R^2$ in general formula (1) is a methyl group. In addition, it is suitable for the solubilization method to combine and use as necessary one, two or more of the purification protocols described above.

Advantageous Effects of Invention

Since the novel thiosulfonate compound of the present invention has a constitution such as described above, it can reversibly cationize a wider range of proteins and peptides with high stability of quality and accuracy, is useful for purification and recovery at high degree, and is a compound that is extremely excellent as a reversible cationization agent for protein and/or peptide. Methods for solubilizing a protein and/or a peptide using such reversible cationization agent are useful in both basic research and clinical fields, such as application to analysis of intracellular proteins, reagents and drugs for studies characterized in that a protein is introduced into a cell, and use of a cell given an artificial function by introducing a protein with the present method, and moreover cancer immunotherapy which introduces an antigenic protein into dendritic cells or an organism, hence it is thought that the application range of chemical research, medical treatments or the like is broad.

BRIEF DESCRIPTION OF DRAWINGS

FIG. 2 is a figure explaining the Solubility Index, which predicts the solubility of the cationized denatured protein.

FIG. 4 shows the analytical results for hen egg-white lysozyme (HEL) which was denatured and cationized reversibly with TAPS-Sulfonate (T1), a conventional reversible cationization reagent, and, TAP3S-Sulfonate (T3), a novel thiosulfonate compound of the present invention, respectively.

FIG. 7 shows the solubility by the two-stage dialysis protocol described in FIG. 6 of the denatured total intracellular protein.

FIG. 8 shows the results from using TAP3S-Sulfonate in the procedure indicated in FIG. 6 to cationize the total protein contained in human epidermoid carcinoma-derived cell line A431 and mouse melanoma B16-F10 cell and prepare a lysate in physiological saline, and quantitating the proteins contained therein by Western blotting (W.B.) using anti-β-tubulin antibody, anti-EGF receptor antibody, anti-TRP2 antibody and anti-gp100 antibody.

FIG. 9 shows the results from disrupting mouse melanoma B16-F10 cell by freeze-thawing in phosphate-buffered physiological saline (PBS) and fractionating to obtain a soluble fraction and an insoluble fraction, and quantitating the amounts of gp100 protein contained therein by Western blotting (W.B.) using anti-gp100 antibody. In the figure, (1) to (4) correspond to lanes 1 to 4 of the W.B.

DESCRIPTION OF EMBODIMENTS

Figure 1:
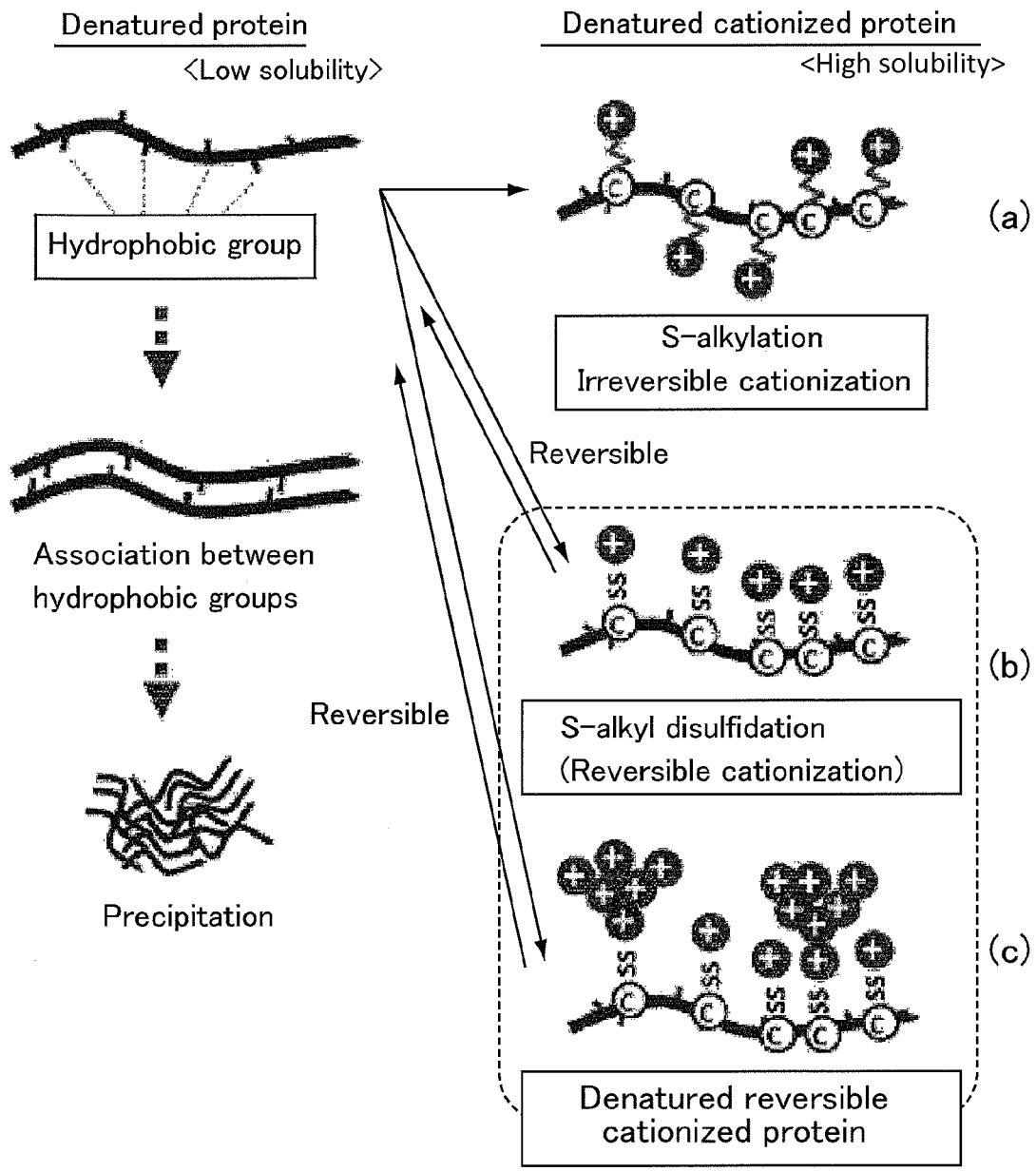
FIG. 1 is a conceptual view showing an example of prior art technique, which shows that proteins dissolved in a denaturing agent (FIG. 1, upper left) associate and become insoluble in water in the absence of a denaturing agent (FIG. 1, lower left), and if hydrophilicity in excess of the hydrophobicity of the denatured proteins is conferred by cationization, high solubility in water is conferred (FIG. 1 right).
Figure 3:
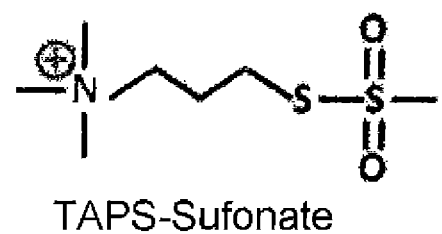
FIG. 3 shows the chemical structural formula of TAPS-Sulfonate, an example of conventional reversible cationization reagent.

Hereafter, the present invention will be described in further detail by giving examples; however, the present invention is not limited only to the examples. Unless explicitly stated otherwise, "%" means "mol %".

Example 1

Synthesis of Novel Cationization Reagent (TAP3S-Sulfonate)

The synthesis of the novel compound of the present invention TAP3S-Sulfonate was carried out according to the schemes indicated by general formulae (i) to (iii). A concrete description is given below.

[Chem. 2]

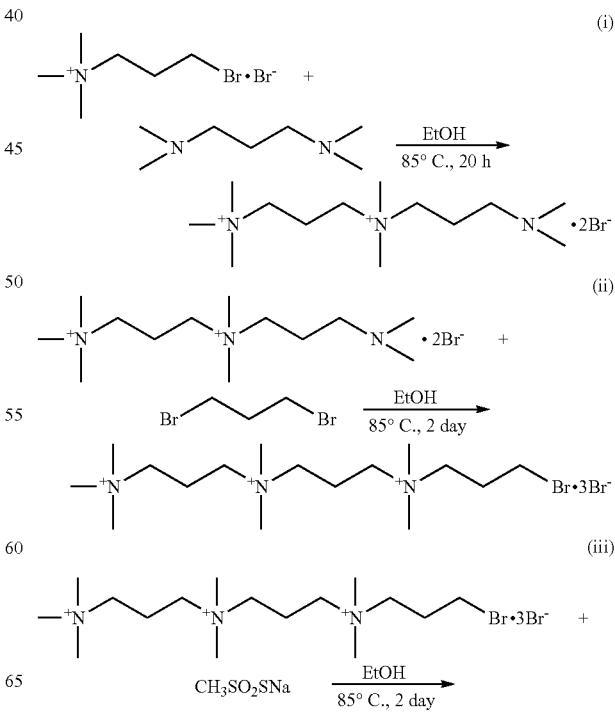

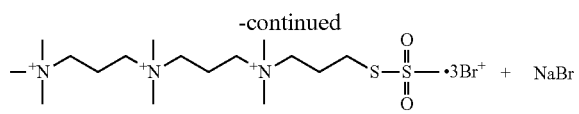

The reaction of the general formula (i) was as follows:

35.1 g (134 mmol) of TAP-Br ((3-bromopropyl)trimethylammonium bromide, J. Biochem., 116, 852-857 (1994)) was weighed out and dissolved in 500 ml of ethanol, 87.5 g (672 mmol) of N,N,N',N'-tetramethyl-1,3-diaminopropane was added and $(CH_3)_3N^+CH_2CH_2CH_2N^+(CH_3)_2CH_2CH_2CH_2N(CH_3)_2 \cdot 2Br^-$ was obtained by reacting at 85° C. for 20 hours while refluxing. Yield amount: 113 mmol (yield 86%).

The reaction of the general formula (ii) was as follows:

40.89 g (104.5 mmol) of $(CH_3)_3N^+CH_2CH_2CH_2N^+(CH_3)_2CH_2CH_2CH_2N(CH_3)_2 \cdot 2Br^-$ was weighed and dissolved in 500 ml of ethanol, 100 ml (979 mmol) of 1,3-dibromopropane was added, and TAP3-Br was obtained by reacting at 85° C. while refluxing for 2 days. Yield amount: 68.8 mmol (yield: 66%).

The reaction of the general formula (iii) was as follows:

31.37 g (52.9 mmol) of TAP3-Br was weighed out and dissolved in 500 ml of ethanol, 7.096 g (52.9 mmol) of $CH_3SO_2SNa$ was added and TAP3S-Sulfonate was obtained by reacting at 85° C. while refluxing for 2 days. The product was confirmed by NMR.

$^1$H-NMR (300 MHz, D2O): δ 3.57-3.33 (m, 10H), 3.50 (s, 3H), 3.30 (t, J=6.8 Hz, 2H), 3.15 (s, 6H), 3.14 (ds, 15H), 2.40-2.18 (m, 6H)

Yield amount: 30 mmol (yield 56%)

Experimental Example 1

Reactivity with Protein and Physical Property Evaluation of TAP3S-Sulfonate

With hen egg-white lysozyme (HEL, molecular weight: 14.3 kDa, 8 Cys residues/mol) serving as a model protein, capability comparison was carried out between TAPS-sulfonate (conventional cationization reagent described in Non-Patent Literature 3 and 4 and the like) and the TAP3S-Sulfonate (novel cationization agent) prepared in Example 1.

10 mg of HEL was dissolved in 1 ml of 6M guanidine hydrochloride, 0.1 M Tris-HCl and 1 mM EDTA pH 8.5; degassing and nitrogen substitution were carried out. Next, 5 mg (0.03 mmol) of Dithiothreitol (DTT) was added, after a reduction reaction at 37° C. for 90 minutes, TAPS-sulfonate or TAP3S-Sulfonate was each added so as to have 3-fold molar amounts of DTT, and reacted at 37° C. for 30 minutes. For the obtained reaction solution, dialysis was carried out thoroughly against pure water and the denatured reversibly cationized HEL obtained in the soluble fraction was used to carry out physical property evaluation. Analysis of each sample was carried out by SDS-PAGE, and, as a result, both TAPS-sulfonate and TAP3S-Sulfonate were found to be bonded quantitatively to the protein through an SS bond (refer to FIG. 4A).

In addition, when reverse-phase HPLC (C18 column) was used and elution was carried out with a linear concentration gradient of acetonitrile, the elution time was shortened in when cationization was performed with TAP3S-Sulfonate, confirming that hydrophilicity was improved (refer to FIG. 4B). Further, when refolding was carried out in a redox system that uses glutathione denatured reversibly cationized HEL of both TAPS-sulfonate and TAP3S-Sulfonate on the order of 90% re-activation rate (Note 1) was obtained for both, suggesting that, with the present reagent, no side-reaction had proceeded other than the chemical modification through SS bond (refer to FIG. 4C).

Note 1: While the egg-white lysozyme in the active conformation has four sets of SS bonds present within one molecule such that there is the necessity of refolding in the correct combination, since the egg-white lysozyme in the active conformation is to be the structure with the lowest free energy (=stable), the molecule in which, ultimately, the cationizing agents having dissociated, the correct four sets of SS bonds have been formed, manifests a biological activity. The "refolding rate" in the present experiment was evaluated with the bacteriolytic activity (enzymatic activity) exhibited by the lysozyme.

Experimental Example 2

Demonstration Experiment for Solubilization Technique for Insoluble Protein

As expected also from the Solubility Index described in FIG. 2, solubility in denatured state is extremely low for a protein containing a multitude of hydrophobic residues. With human β Actin (refer to Table 1) serving as one such model protein, a verification experiment for the solubilization by denatured reversible cationization was proceeded. The amino acid composition of human β Actin protein is shown in Table 1.

TABLE 1

| | |
|---|---|
| Molecular weight | 43.3 kDa |
| The number of hydrophobic residue (W, I, L, F) | 72 (per molecule) |
| Positively charged amino acid (In the case of pH5, K, R, H) | 48 (per molecule) |
| Negatively charged amino acid (In the case of pH5, D, E) | 49 (per molecule) |
| Cys capable of being subjected to denatured reversible cationization reaction | 6 (per molecule) |

Here, when calculating the Solubility Index (SI) of human β Actin at pH 5, it is done in the following manner, and from the property that dissolving is facilitated when a large negative or positive value is displayed, the case where cationization is performed with TAP3S-Sulfonate is anticipated to be the most advantageous solubility.

Unmodified: SI=(48-49)/72=-0.014

T1 (TAPS-modified): SI (TAPS-modified)=(48-49+6)/72=+0.07

T3 (TAP3-modified): SI (TAP3-modified)=(48-49+18)/72=+0.236

The demonstration experiment was carried out as follows:

When centrifugal separation was carried out after bacteriolysis by sonication, human β Actin expressed in *Escherichia coli* was recovered as an insoluble fraction (inclusion body); at this time point, 90% or greater purity was observed in an analysis by SDS-PAGE. This human β Actin was dissolved in 6 M guanidine hydrochloride, DTT was added so as to have 30 mM final concentration and treated at 37° C. for 2 hours, thereby reducing the protein completely. Next, TAPS-sulfonate and TAP3S-Sulfonate were added so that the final concentrations were 90 mM respectively, reacted at 37° C. for 30 minutes, then, dialysis was carried out thoroughly against pure water, thereby to obtain denatured reversibly cationized β Actin.

The solubility of each sample was evaluated by measuring the absorbance at 280 nm and 320 nm (refer to Table 2). As a result, while denatured reversibly cationized β Actin from both were soluble present in pure water, the absorption at 320 nm was relatively high for the TAPS-modified β Actin protein, suggesting that aggregation has been proceeding in the solvent. The solubility of denatured reversibly cationized β Actin protein in pure water (absorption after 4-fold dilution) is shown in Table 2.

TABLE 2

|  | T1: TAPS-modified Actin | T3: TAP3-modified Actin |
| --- | --- | --- |
| ABS280 (absorbance of protein) | 0.79 | 0.707 |
| ABS320 (aggregation index of protein) | 0.143 | 0.085 |

Next, experiments were carried out under the following conditions A to C for dissolving in physiological saline (0.15M NaCl) the denatured reversibly cationized β Actin protein that has been dissolved in pure water. The conditions A to C are shown in Table 3.

TABLE 3

| | |
| --- | --- |
| A | A 0.3M NaCl solution with pH of 5.5 and each modified β actin solution were mixed in the ratio 1:1 and the mixture was allowed to stand for 30 minutes. The mixture was centrifuged at 10,000 rpm for 5 minutes. The absorbance of an soluble fraction was determined. |
| B | A solvent of each modified β actin solution was replaced by 0.15M physiological saline using gel filtration chromatography (Nap5 column, GE health care) that was balanced with 0.15M physiological saline (pH 5.5). The solution was centrifuged at 10,000 rpm for 5 minutes. The absorbance of an soluble fraction was determined. |
| C | Each modified β actin solution was subjected to separation and purification by linear concentration gradient elution with 1 to 80% acetonitrile in the presence of 0.1% hydrochloric acid using reversed phase HPLC (capsule pack C1, Shiseido Co., Ltd.), and was freeze-dried. Protein obtained after the freeze-drying was dissolved in a small amount of pure water, and a solvent was prepared to be 0.15M physiological saline. The resulting samples each were centrifuged at 10,000 rpm for 5 minutes. The absorbance of an soluble fraction was determined. |

Evaluation results of the solubility in physiological saline of the denatured reversibly cationized β Actin protein prepared with the purification conditions of A to C are compiled in Table 4. As it is also apparent from this result, it was confirmed that, while solubilization was almost not possible with the TAPS-modification of the conventional type, satisfactory solubilization was possible with the TAP3S-modification using the novel reagent of the present invention. In addition, it was confirmed that, if the protein was purified to high-purity using reverse-phase HPLC, hydration was readily possible also from a solid body after freeze-drying, and, the protein existed in an ideal dissolution state, with aggregation in solution also being suppressed to extremely low levels. The relationship between the solubility of the denatured reversibly cationized β Actin protein in physiological saline and the sample preparation method is shown in Table 4.

TABLE 4

| Preparation condition | T1: TAPS-modified β Actin | | T3: TAP3S-modified β Actin | |
| --- | --- | --- | --- | --- |
| | ABS 280 | ABS280/ ABS320 | ABS 280 | ABS280/ ABS320 |
| A: Dialysis | 0 (all insolubilized) | — | 0.343 | 14.3 |
| B: Gel filtration purification | 0 (all insolubilized) | — | 0.972 | 13.5 |
| C: HPLC purification | 0 (all insolubilized) | — | 0.814 | 22.0 |

While the mechanism whereby the solubility increases widely through reverse-phase column purification is being analyzed, the species of counter ion and elimination of small molecule contaminants (such as methanesulfinic acid) are thought to be the keys. This paves the way for enhanced solubility of the denatured reversibly cationized protein.

Experimental Example 3

Application to Solubilization Technique for Intracellular Total Protein, 1

In order to develop a technique for solubilizing entirety the total protein in cancer cells or the like, the effectiveness of the present reagent was verified. With living tissues such as cancer cells serving as materials, when cationizing proteins contained therein, it was clear that nucleic acids contained in large amounts in living tissues, as they possess strongly negative electric charges, electrostatically associate with and insolubilize the cationized protein.

Figure 5:
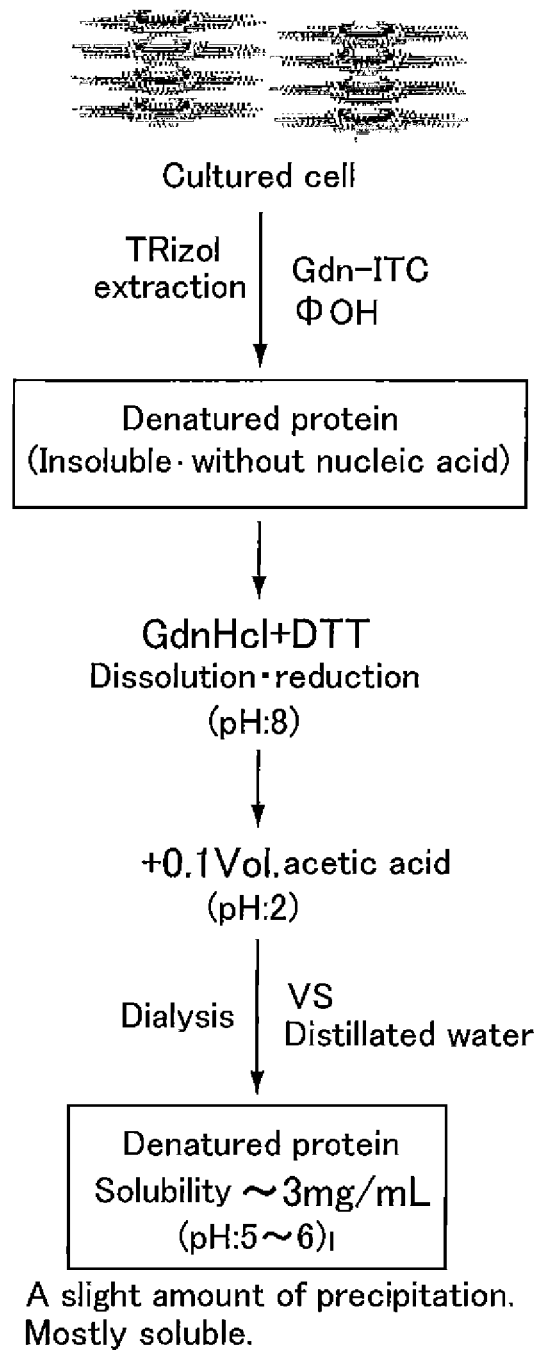
FIG. 5 shows an example of processing conditions allowing total protein extracted from a cell to retain high water solubility still in denatured state.

Thus, it was decided to apply the Trizol reagent (phenol/ guanidine isothiocyanate; manufactured by Invitrogen), which allows nucleic acids and proteins to be separated/ purified quantitatively from living tissues, to extract nucleic acid-free total protein. In order to examine the solubilization conditions for the denatured proteins acquired with this technique, when the total protein was treated with the technique shown in FIG. 5, mixtures of unmodified denatured proteins were found to dissolve adequately in water. Such observations related to the solubility of denatured proteins, while not thought to have been reported, are inferred to be those of intrinsic properties demonstrated by intracellular proteins of eukaryotes, and are extremely interesting observations protein-scientifically. While mouse B16 melanoma was used as the cultured cell of FIG. 5, the results were almost the same when other human cancer cells (HeLa, A431, or the like) were used.

With regard to the intracellular total protein extracted using the Trizol reagent, after dissolving with 6 M guanidine hydrochloride, cationization reactions with TAPS-sulfonate and TAP3S-Sulfonate respectively were carried out by the method described previously; however, the respectively cationized proteins could not demonstrate high solubility in physiological saline. Thus, taking as a reference the fact that the process of eliminating contaminants by reverse-phase column purification contributed to solubility-improvement in the examination of the solubilization conditions for the β Actin protein described previously, the two-stage dialysis protocol indicated in FIG. 6 was developed.

As a result of these examinations, the intracellular total protein treated by the two-stage dialysis protocol was confirmed to demonstrate high solubility also in physiological saline by the reversibly-denaturing-cationizing method (refer to FIG. 7). In particular, the solubility almost not decreasing even in physiological saline, the proteins cationized with TAP3S-Sulfonate were confirmed to be of extremely high usefulness in case there is a necessity of maintaining physiological conditions of a cell, such as when adding them to cultured cell.

Experimental Example 4

Application to Solubilization Technique for Intracellular Total Protein, 2

Figure 6:
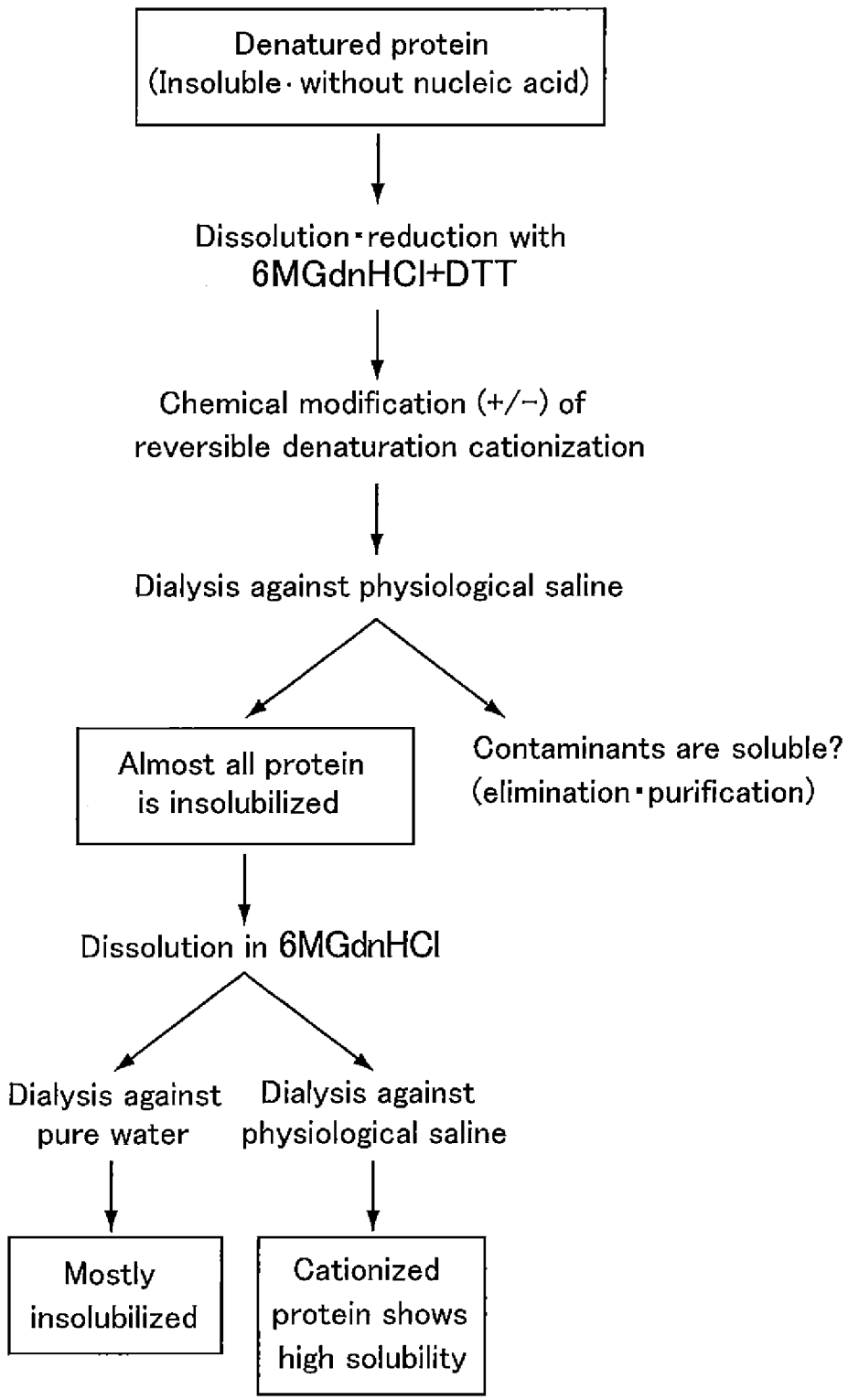
FIG. 6 shows an example of two-stage dialysis protocol whereby denatured total intracellular protein is solubilized in physiological saline to a high degree.

(1) Lysates were prepared, comprising the total proteins contained in human epidermoid carcinoma-derived cell line A431 and mouse melanoma B16-F10 cell, which were cationized using TAP3S-Sulfonate by the procedure indicated in FIG. 6 and dissolved in physiological saline. The proteins contained in the respective lysates were quantified by Western-blotting (W.B.) using anti-β-tubulin antibodies (Cell signaling Technology: #2146), anti-EGF receptor antibodies (manufactured by Sigma: E2760), anti-TRP2 antibodies (manufactured by Santa cruz biotechnology: SC-25544) and anti-gp100 antibodies (manufactured by Santa cruz biotechnology: SC-33590). As a result, antigen proteins corresponding to these antibodies were confirmed to be dissolved (refer to FIG. 8). It was confirmed that, by applying the present technique, dissolving completely the total protein contained inside a cancer cell in physiological saline was possible and that each antigen among EGF receptor, TRP2 and gp100, which are actually known as cancer antigen proteins, were dissolved. The present technique can be claimed to be a strong technique also in preparing a vaccine for cancer treatment from a cancer cell.

(2) For comparison purposes, by way of a freeze-thawing method, which repeats five times freezing at −80° C. and melting at 37° C. the interior of a mouse melanoma B16-F10 cell in phosphate-buffered saline (PBS), cells were disrupted, then, fractionated by centrifugal separation into a soluble fraction and an insoluble fraction, and the amount of gp100 protein that each contains was quantified by Western blotting (W.B.) using anti-gp100 antibodies (manufactured by Santa cruz biotechnology: SC-33590). As a result, it was confirmed that approximately 50% of the cancer antigen protein gp100 became insoluble after freeze-thawing (refer to FIG. 9).

The invention claimed is:

1. A thiosulfonate compound having within one molecule three or more cations derived from a quaternary ammonium group.

2. The thiosulfonate compound according to claim 1, represented by the following general formula (1):

[Chem. 1]

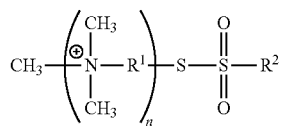

(1)

(wherein $R^1$ is identical or different from one another and represents an alkylene group having 2 to 20 carbons; $R^2$ represents a lower alkyl group; and n is an integer of 3 to 10).

3. The thiosulfonate compound according to claim 2, wherein $R^1$ in the general formula (1) is a linear alkylene group having 2 to 6 carbons.

4. The thiosulfonate compound according to claim 3, wherein the $R^1$ is a propylene group.

5. The thiosulfonate compound according to claim 2, wherein n in the general formula (1) is 3.

6. The thiosulfonate compound according to claim 2, wherein $R^2$ in the general formula (1) is a methyl group.

7. A reversible cationization agent for reversibly-cationizing a protein and/or a peptide, the reversible cationization agent containing the thiosulfonate compound according to claim 1.

8. A method for protein and/or peptide solubilization which comprises reacting the reversible cationization agent according to claim 7 with the protein and/or peptide.

9. The method for protein and/or peptide solubilization according to claim 8, wherein the protein and/or the peptide are denatured protein and/or peptide.

10. A method for solubilization for solubilizing a mixture of denatured total protein extracted from a cultured cell and/or a living tissue in a physiological salt solution, wherein the solubilization method comprises reacting the reversible cationization agent according to claim 7 with the mixture of denatured total protein extracted from a cultured cell and/or a living tissue in a physiological salt solution.

11. The thiosulfonate compound according to claim 3, wherein n in the general formula (1) is 3.

12. The thiosulfonate compound according to claim 4, wherein n in the general formula (1) is 3.

13. The thiosulfonate compound according to claim 3, wherein $R^2$ in the general formula (1) is a methyl group.

14. The thiosulfonate compound according to claim 4, wherein $R^2$ in the general formula (1) is a methyl group.

15. The thiosulfonate compound according to claim 5, wherein $R^2$ in the general formula (1) is a methyl group.

16. A reversible cationization agent for reversibly-cationizing a protein and/or a peptide, the reversible cationization agent containing the thiosulfonate compound according to claim 2.

17. A reversible cationization agent for reversibly-cationizing a protein and/or a peptide, the reversible cationization agent containing the thiosulfonate compound according to claim 3.

18. A reversible cationization agent for reversibly-cationizing a protein and/or a peptide, the reversible cationization agent containing the thiosulfonate compound according to claim 4.

19. A reversible cationization agent for reversibly-cationizing a protein and/or a peptide, the reversible cationization agent containing the thiosulfonate compound according to claim 5.

20. A reversible cationization agent for reversibly-cationizing a protein and/or a peptide, the reversible cationization agent containing the thiosulfonate compound according to claim 6.

* * * * *